US009433386B2

United States Patent
Mestha et al.

(10) Patent No.: US 9,433,386 B2
(45) Date of Patent: Sep. 6, 2016

(54) METHOD AND APPARATUS FOR MONITORING A SUBJECT FOR ATRIAL FIBRILLATION

(71) Applicant: Xerox Corporation, Norwalk, CT (US)

(72) Inventors: Lalit Keshav Mestha, Fairport, NY (US); Survi Kyal, Rochester, NY (US); Barry P. Mandel, Fairport, NY (US); Peter Johan Nystrom, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 239 days.

(21) Appl. No.: 13/937,740

(22) Filed: Jul. 9, 2013

(65) Prior Publication Data

US 2015/0018693 A1 Jan. 15, 2015

(51) Int. Cl.
*A61B 6/00* (2006.01)
*A61B 5/00* (2006.01)
*A61B 5/024* (2006.01)

(52) U.S. Cl.
CPC ........... *A61B 5/7282* (2013.01); *A61B 5/0024* (2013.01); *A61B 5/02427* (2013.01); *A61B 5/6831* (2013.01); *A61B 5/0022* (2013.01); *A61B 5/746* (2013.01)

(58) Field of Classification Search
CPC .............. A61B 5/0022; A61B 5/0024; A61B 5/02427; A61B 5/6831; A61B 5/7782; A61B 5/746
USPC .................................................. 600/473–480
See application file for complete search history.

(56) References Cited

U.S. PATENT DOCUMENTS

| 7,177,686 B1* | 2/2007 | Turcott ........................... 607/23 |
| 7,324,848 B1* | 1/2008 | Turcott ........................... 607/17 |
| 8,780,786 B2* | 7/2014 | Shoaib et al. ................ 370/317 |
| 2013/0138002 A1* | 5/2013 | Weng et al. .................. 600/508 |

OTHER PUBLICATIONS

Abo Alam, Kawther, "Fuzzy Logic Hemoglobin Sensors", Karlsruhe Institute of Technology, May 10, 2011.
Buinevicius et al., "A Three-Wavelength Pulse Oximeter for Carboxyhemoglobin Determination", Journal of Iranian Association of Electrical and Electronics Engineers, vol. 5, No. 2, 2008.
Kyal et al., "Continuous Cardiac Pulse Rate Estimation From Multi-Channel Source Video Data", U.S. Appl. No. 13/528,307, filed Jun. 20, 2012.

(Continued)

*Primary Examiner* — Sanjay Cattungal
(74) *Attorney, Agent, or Firm* — Philip E. Blair; Fleit Gibbons Gutman Bongini & Bianco P.L.

(57) ABSTRACT

What is disclosed is a method for monitoring a subject for cardiac arrhythmia such as atrial fibrillation using an apparatus that can be comfortably worn by the subject around an area of exposed skin where a photoplethysmographic (PPG) signal can be registered. In one embodiment, the apparatus is a reflective or transmissive wrist-worn device with emitter/detector pairs fixed to an inner side of a band with at least one illuminator emitting source light at a specified wavelength band. The illuminator is paired to a respective photodetector comprising one or more sensors that are sensitive to a wavelength band of its paired illuminator. The photodetector measures intensity of sensed light emitted by a respective illuminator. The signal obtained by the sensors comprises a continuous PPG signal. The continuous PPG signal analyzed for peak-to-peak pulse points from which the existence of cardiac arrhythmia such as atrial fibrillation event can be determined.

36 Claims, 8 Drawing Sheets

(56) References Cited

OTHER PUBLICATIONS

Kyal et al., "Continuous Cardiac Pulse Rate Estimation From Multi-Channel Source Video Data With Mid-Point Stitching", U.S. Appl. No. 13/871,728, filed Apr. 26, 2013.

Kyal et al., "Continuous Cardiac Signal Generation From a Video of a Subject Being Monitored for Cardiac Function", U.S. Appl. No. 13/871,766, filed Apr. 26, 2013.

Zephyr Technology, "Zephyr BioHarness 3 Data Sheet", 2012, pp. 1-16.

Zwart et al., "Multicomponent Analysis of Hemoglobin Derivatives with a Reversed-Optics Spectrophotometer", Clinical Chemistry, vol. 30, No. 3, 1984, pp. 373-379.

Sola et al., "Validation of a wrist monitor for accurate estimation of RR intervals during sleep", 35th Annual International Conference of the IEEE EMBS, Jul. 3, 2013, pp. 5493-5496.

* cited by examiner

METHOD AND APPARATUS FOR MONITORING A SUBJECT FOR ATRIAL FIBRILLATION

CROSS REFERENCE TO RELATED APPLICATIONS

This patent application is related to concurrently filed and commonly owned U.S. patent application Ser. No. 13/937,782, "Method And Apparatus For Monitoring A Subject For Functional Blood Oxygen Saturation", by Mandel et al., and U.S. patent application Ser. No. 13/937,949, "Method And Apparatus For Monitoring A Subject For Fractional Blood Oxygen Saturation", by Mestha et al., both of which are incorporated herein in their entirety by reference.

TECHNICAL FIELD

The present invention is directed to an apparatus that can be worn circumferentially around an area of exposed skin of a subject being monitored for the presence of atrial fibrillation.

BACKGROUND

Atrial fibrillation (A-fib) is a common cardiac arrhythmia which can cause palpitations, fainting, and chest pain. Even brief A-fib episodes are associated with risks for stroke, heart failure, hospitalization, and death. It is one of the most common arrhythmias which increases with age and presents with a wide spectrum of symptoms.

Most A-fib detection methods rely on a variability of the RR interval from electrocardiogram (ECG) signals. Chaos and randomness of fluctuations of the stroke volumes of the heart muscle can lead to relatively large fluctuations in the levels of the systolic and the diastolic pressure waves. The asymptomatic nature of A-fib makes it difficult to detect. Frequent monitoring can help to improve detection and minimize the associated risks. Therefore, there is a need for new technologies for detecting the presence of A-fib which can be worn by a patient so that monitoring can be done without impacting the patient's quality of life. Cost effective A-fib monitoring devices are desired. There is a need for such devices that can be worn in the home or work environment for continuous A-fib monitoring and physiological event detection.

Accordingly, what is needed in this art is a method and apparatus for monitoring a subject of interest for atrial fibrillation which can be comfortably worn by the subject circumferentially around an area of exposed skin.

BRIEF SUMMARY

What is disclosed is a method and apparatus for monitoring a subject of interest for atrial fibrillation which can be comfortably worn by the subject around an area of exposed skin such as the wrist or ankle. An embodiment of a reflective sensing apparatus and a transmissive sensing apparatus are disclosed for atrial fibrillation (A-Fib) monitoring. Each embodiment comprises at least one emitter/detector pair fixed to an inner side of a band worn circumferentially around an area of exposed skin of a subject such as, for instance, the wrist. The emitter comprises at least one illuminator with the illuminator emitting light at a specified wavelength band. More than one emitter/detector pair may be introduced to improve the signal strength. In one embodiment where the present apparatus comprises a transmissive sensing device, each photodetector measures an intensity of light emitted from its respective paired illuminator which has passed through a chord of living tissue. In another embodiment where the present apparatus comprises a reflective device, each photodetector measures an intensity of light emitted from its respective paired illuminator which has reflected off a surface of the skin. In each configuration, a time-series signal is generated by the continuous sensing of light intensities. Any one emitter-detector pair is adequate to obtain pulsating time-series signal. If emitters of similar wavelength are selected, then average time-series signal is obtained by averaging signal coming out of two detectors of two emitter/detector pairs of similar wavelengths. The time-series signal comprises a continuous PPG signal of the subject. In another embodiment, the time-series signal is processed to extract the continuous PPG signal. Both embodiments are disclosed herein in detail. The continuous PPG signal is analyzed to determine the presence of atrial fibrillation. Alert signals can be communicated to one or more remote devices such as, a smartphone, if the A-fib episode falls outside a limit of acceptability which has been pre-set for this subject.

Many features and advantages of the above-described apparatus will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for monitoring a subject of interest for atrial fibrillation using an apparatus that can be comfortably worn by the subject circumferentially around an area of exposed skin.

Non-Limiting Definitions

A "subject of interest" refers to a subject having a cardiac function. Although the term "human", "person", or "patient"

may be used throughout this disclosure, it should be appreciated that the subject may not be human. As such, use of the terms "human", "person" or "patient" is not to be viewed as limiting the scope of the appended claims strictly to human beings.

Figure 1:
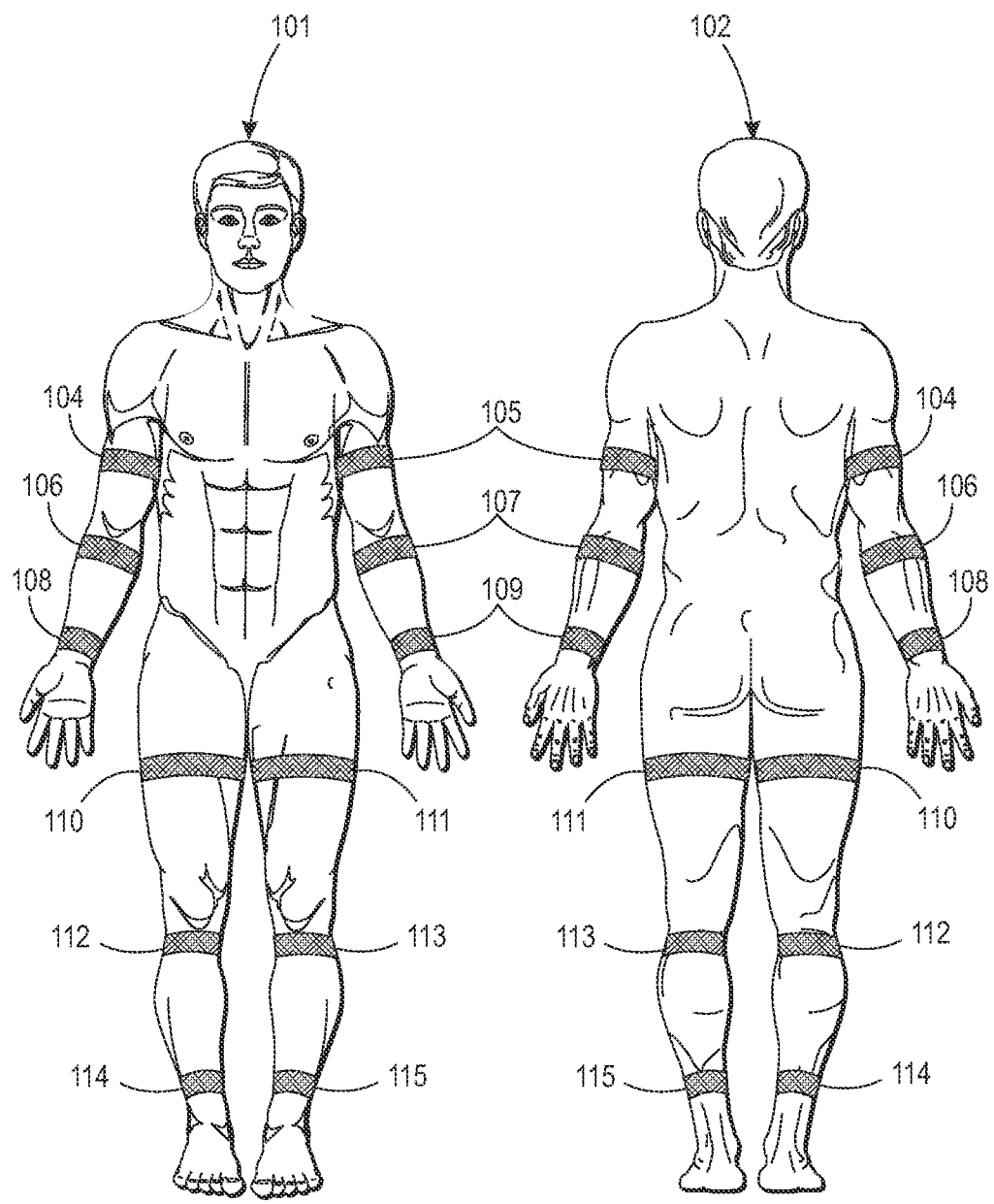
FIG. 1 illustrates an anterior and dorsal view of a subject of interest to show various locations where the present apparatus is likely to be worn.
Figure 2:
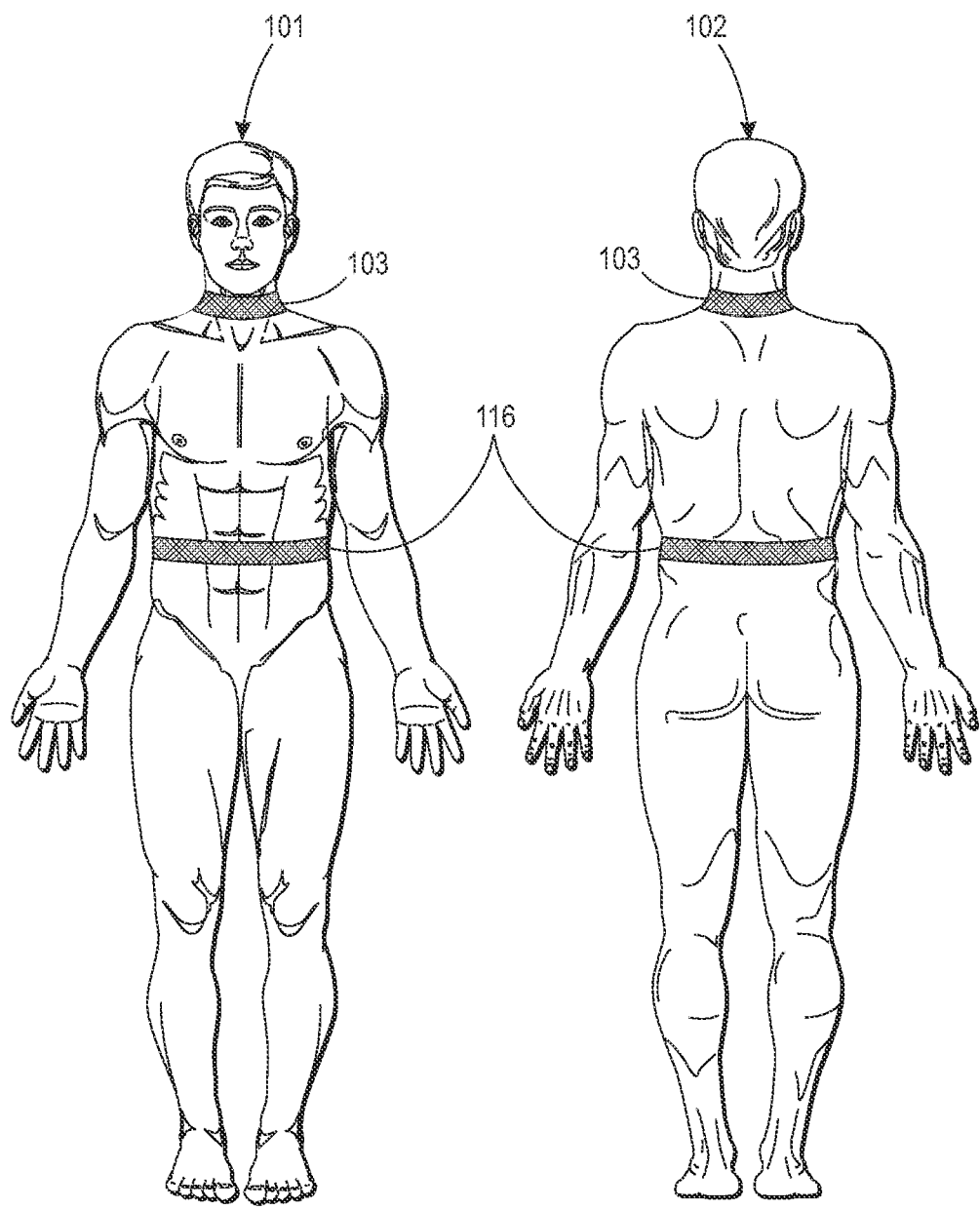
FIG. 2 illustrates the anterior and dorsal views of the subject of FIG. 1 showing that the present apparatus can also be worn circumferentially around the neck and circumferentially around an area of the subject's mid-section.
Figure 3:
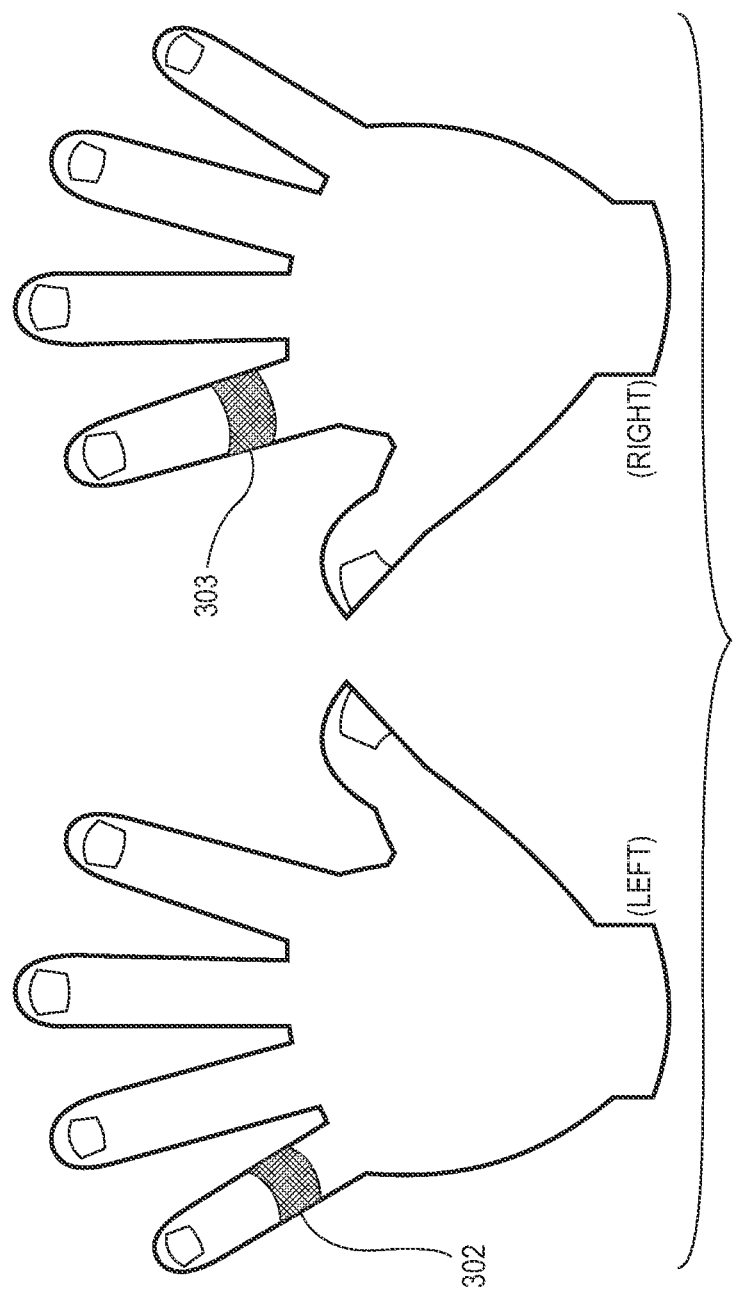
FIG. 3 shows an embodiment of the present apparatus being worn circumferentially around a finger of each of the subject's left and right hands.

An "area of exposed skin" refers to a circumferential region of the subject where a photoplethysmographic (PPG) signal can be obtained by various embodiments of the apparatus disclosed herein. FIG. 1 illustrates an anterior view 101 of a subject of interest and a dorsal view 102. Various circumferential areas of exposed skin are shown where the present apparatus is likely to be worn. For example, the present apparatus can be worn circumferentially around the upper left or right arms at 104 and 105, respectively. Or, around the left or right forearms at 106 and 107; around the left or right wrists at 108 and 109; around the upper left and right thigh at 110 and 111; around the left and right calf at 112 and 113; or around the left and right ankle at 114 and 115. FIG. 2 illustrates the anterior and dorsal views of the subject of FIG. 1 showing that the present apparatus can also be worn circumferentially around the neck 103 and around an area of the mid-section 116 where PPG signals can be registered. The illustrations of FIGS. 1 and 2 should not be viewed as limiting the scope hereof to the areas shown, as other embodiments of the present apparatus can be worn circumferentially around the finger, toe, forehead, hand, and foot. FIG. 3 shows an embodiment of the present apparatus being worn circumferentially around a finger 302 of the subject's left hand or around a finger 303 of the subject's right hand.

"Cardiac arrhythmia", also known as cardiac dysrhythmia, is an irregular heartbeat caused by a change in the heart's electrical conduction system.

"Atrial fibrillation" (A-fib or AF), is a common cardiac arrhythmia. In A-fib patients, the normal regular electrical impulses generated by the sinoatrial node of the heart are overwhelmed by disorganized electrical impulses usually originating in the roots of the pulmonary veins, leading to irregular conduction of impulses to the ventricles which generate the heartbeat. In A-fib, the P-waves, which represent depolarization of the atria, are absent or unmeasurable using the ECG, with unorganized electrical activity in their place. The A-fib patient has irregular R-R intervals due to irregular conduction of impulses to the ventricles. Irregular R-R intervals may be difficult to determine if the rate is rapid. A-fib increases the risk of heart attack or stroke, depending on the presence of additional risk factors such as, for instance, high blood pressure and a narrowing of the mitral valve of the heart ("mitral stenosis"). A-fib may occur in episodes lasting from minutes to days and may even be permanent. A-fib may be treated with medications to either slow the heart rate to a normal range ("rate control") or revert the heart rhythm back to normal ("rhythm control"). The evaluation of atrial fibrillation involves diagnosis, determination of the etiology of the arrhythmia, and classification.

"Photoplethysmography" is the study of signals containing relative blood volume changes in vessels which are close to the skin surface. Sensors of the present apparatus using sequentially captured pulsating signals provide a continuous time-series signal which, in one embodiment, is the subject's PPG signal. In other embodiments, the time-series signal is processed to extract the PPG signal. In this alternative embodiment, a sliding window is used to define consecutive time-sequential segments of the time-series signal. Each signal segment overlaps a previous segment by at least a 95%. Each of the consecutive time-series signal segments is detrended to remove low frequency variations and non-stationary components. The detrended signal segments are filtered such that frequencies of the subject's cardiac beat are retained. In one embodiment, the filter comprises a higher-order band-limited Finite Impulse Response (FIR) Filter which constrains band width to a desired range of the subject's heart. The filtered time-series signal segments are then upsampled to a pre-selected sampling frequency to increase a total number of data points in order to enhance the accuracy of peak-to-peak pulse point detection. In one embodiment, upsampling involves an interpolation technique using a cubic spline function and a pre-selected sampling frequency. The upsampled time-series signal segments are then smoothed using any of a variety of smoothing techniques. These processed signal segments are then stitched together to obtain a continuous PPG signal for the subject. Example stitching methods are disclosed in: "Continuous Cardiac Pulse Rate Estimation From Multi-Channel Source Video Data", U.S. patent application Ser. No. 13/528,307, by Kyal et al., "Continuous Cardiac Pulse Rate Estimation From Multi-Channel Source Video Data With Mid-Point Stitching", U.S. patent application Ser. No. 13/871,728, by Kyal et al., and "Continuous Cardiac Signal Generation From A Video Of A Subject Being Monitored For Cardiac Function", U.S. patent application Ser. No. 13/871,766, by Kyal et al., all of which are incorporated herein in their entirety by reference.

"Analyzing a signal" for atrial fibrillation means, in one embodiment, to determine peak-to-peak pulse points in the received signal and analyze those pulse points to determine cardiac pulse dynamics, i.e., across consecutive beats. The pulse dynamics are used to detect the presence of atrial fibrillation. The peak-to-peak pulse points can be detected in the PPG signal using, for instance, an adaptive thresholding technique with successive thresholds being based on variations detected in previous magnitudes of the pulse peaks. The peak-to-peak pulse points may be normalized to a frequency such as, for example, between 60-70 bpm, to reduce pulse variations. A Poincare diagram of the peak-to-peak pulses can be used to determine a relationship between consecutive beats. The presence of A-fib can be detected by examining a time interval between consecutive beats. An alert signal can be sent in response to the A-fib event being outside a pre-defined limit of acceptability. The alert signal may take the form of a text message, an email, a picture, graph, chart, or pre-recorded message. The signal may further include one or more aspects of the subject's PPG signal so that the medical practitioner can view the obtained PPG signal for themself.

An "emitter" refers to an illuminator which emits source light at a desired wavelength band. An emitter may comprise one or more illuminators. The illuminators preferably emit source light at a wavelength range centered around 660 nm because the absorbance of light in the red region of the light spectrum is higher for deoxygenated hemoglobin than for oxygenated hemoglobin. Wavelengths at 940 nm are also considered since the pulsating blood flow can produce pulsing electrical signals at the photodetector. Signal strength of pulsating blood will be high at these wavelengths so peak-to-peak pulse detection will be more accurate and reliable.

A "photodetector" or simply "detector" is a light sensing element comprising one or more sensors or sensing elements which are sensitive to a wavelength band of a respective illuminator system. Each photodetector continuously measures an intensity of received light emitted by its illuminators and outputs, in response thereto, a time-series signal. To improve signal to noise ratio in the time-series signal, in one embodiment, all the emitters at similar wavelength band are illuminated and photodetector outputs combined to produce a single time-series signal. The photodetectors are fixed to an inner side of the band with each emitter/detector pair being separated by a distance D, as discussed with respect to FIGS. 4-6.

Figure 4:
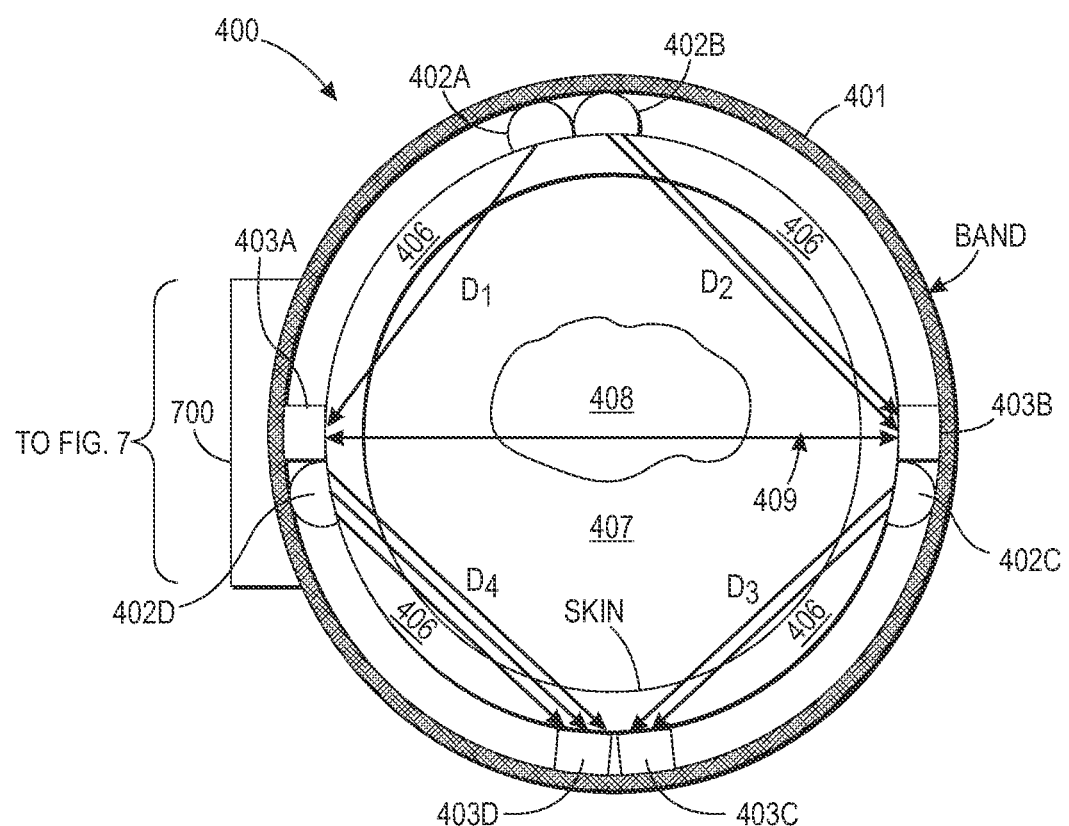
FIG. 4 shows one embodiment of a transmissive device worn circumferentially around an area of exposed skin as shown in any of FIGS. 1-3.

A "transmissive device" is one embodiment of the present apparatus where the distance D separating each illuminator and paired detector defines a chord of living tissue through which the emitted source light passes. The distance D is less than 75% of a diametrical distance of the area around which the apparatus is worn. The respective paired photodetector measures an intensity of light passing through the chord of living tissue. FIG. 4 shows one embodiment of a transmissive device 400 worn circumferentially around an area of exposed skin. Band 401 has a plurality of emitter/detector pairs fixed to an inner side thereof. Emitters 402A-D are paired, respectively, to detectors 403A-D. Emitter 402A comprises a single illuminator which emits light at a desired wavelength band. Emitters 402B and 402C each comprise two illuminators, which may emit light at the same or different wavelength bands. Emitter 402D is shown comprising three illuminators which may all emit source light at a same or different wavelength bands. The band 401 may comprise any configuration of emitter/detector pairs. FIG. 4 is one example. Band 401 is worn circumferentially around an area the skin 406 covering a plurality of subcutaneous tissues (collectively at 407) which surround deeper tissues such as muscles, organs, bones, and the like (collectively at 408). Distances $D_1$, $D_2$, $D_3$ and $D_4$ each define a chord of living tissue through which light emitted by illuminators 402A-D passes and which, in turn, is detected by paired photodetectors 403A-D. Although not illustrated exactly to scale, distance $D_1$, $D_2$, $D_3$, $D_4$ are less than 75% of a diametrical distance 409 of the area around which the apparatus is worn. Distances between respective emitter/detector pairs do not have to be equal. It should be appreciated that the subcutaneous tissues include a plurality of blood vessels and other tissue structures. Other embodiments of the transmissive device hereof comprise multiple emitter/detector pairs fixed to an inner side of the band.

Figure 5:
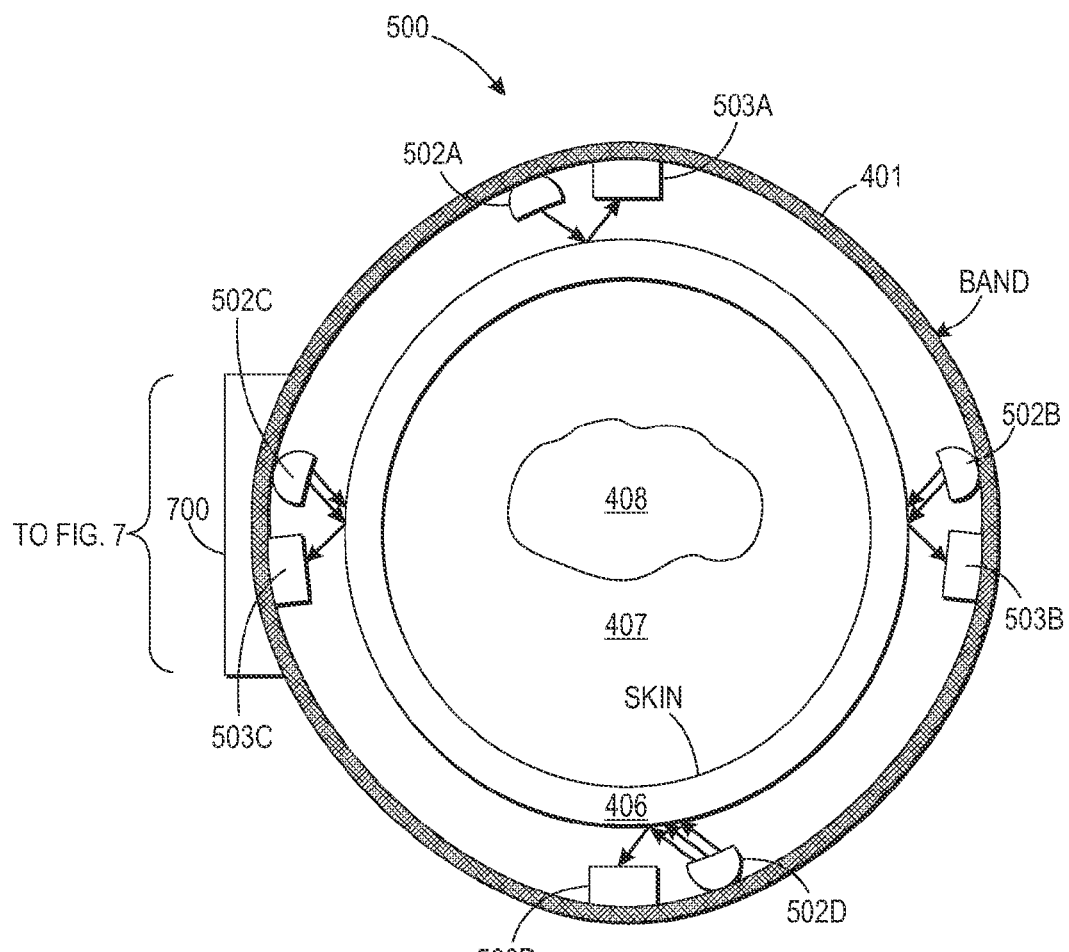
FIG. 5 shows one embodiment of a reflective device worn circumferentially around the area of exposed skin of FIG. 4.
Figure 6:
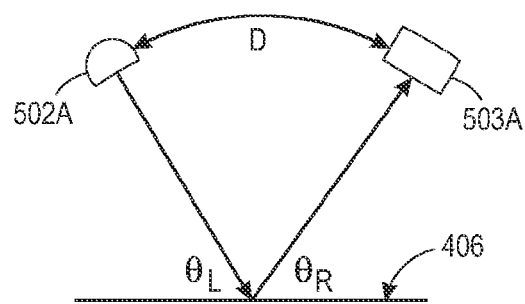
FIG. 6 shows the angular relationships of the emitter/detector pair of the reflective device of FIG. 5.

A "reflective device" is one embodiment of the present apparatus where each photodetector measures an intensity reflecting off a surface of skin 406. FIG. 5 shows one embodiment of a transmissive device 500 worn circumferentially around an area of exposed skin as shown in any of FIGS. 1-3. Band 401 has a plurality of emitter/detector pairs fixed to an inner side thereof. Emitters 502A-D are paired, respectively, to detectors 503A-D. Emitter 502A comprises a single illuminator which emits light at a desired wavelength band. Emitters 502B and 502C each comprise two illuminators, which may emit light at the same or different wavelength bands. Emitter 502D is shown comprising three illuminators which may all emit source light at a same or different wavelength bands. The band 401 may comprise any configuration of emitter/detector pairs. FIG. 5 is one example. Band 401 is worn circumferentially around an area the skin 406 covering a plurality of subcutaneous tissues (collectively at 407) which surround deeper tissues such as muscles, organs, bones, and the like (collectively at 408). It should be appreciated that the subcutaneous tissues include a plurality of blood vessels and other tissue structures. In FIG. 6, the source light emitted by each illuminators 502 impacts the surface of the skin 406 at angle $\theta_L$ and reflects off the skin surface at angle $\theta_R$, where $0° < (\theta_L, \theta_R) < 90°$. Distance D is a distance measured between each illuminator 502 and its paired photodetector 503.

Example Control Panel

Figure 7:
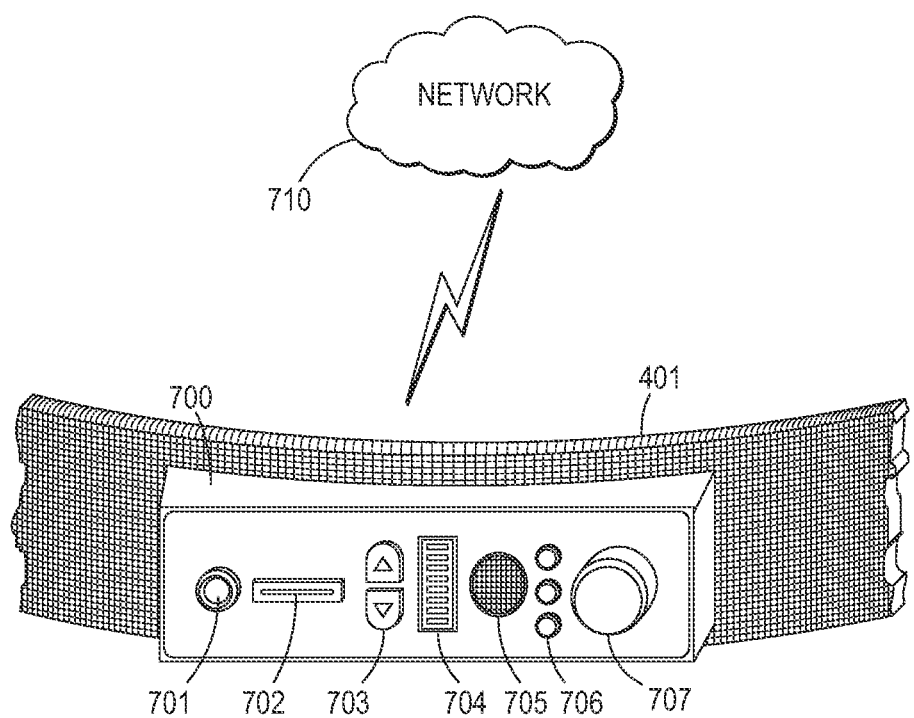
FIG. 7 shows one embodiment of a control panel fixed to an outer side of the bands of each of the transmissive and reflective devices of FIGS. 4 and 5.

Reference is now being made to FIG. 7 which shows one embodiment of a control panel 700 fixed to an outer side of the bands of each of the transmissive and reflective devices of FIGS. 4 and 5. The control panel allows the user to effectuate various aspects of the functionality of the embodiments disclosed herein.

In FIG. 7, the control panel 700 has female adaptor 701 for receiving male counterpart of a power supply, as are normally understood, to charge one or more batteries (not shown). In some embodiments, a separate power supply comprising a battery pack is kept in a pocket and a cord is connected to the control pattern via adaptor 701. The power supply may be a transformer plugged into a wall socket with a cord which provides continuous power to the present apparatus. Also shown is a slot 702 for insertion of a memory chip or MicroSD card as are typically found in cellular smartphone devices. Such a removable memory card records signals obtained from the photodetectors, and may contain device specific parameters which are used to set power levels, adjust intensity values, provide data, formulas, threshold values, patient information, and the like. Once inserted into the device, the present apparatus reads the data as needed. A microprocessor (CPU) or ASIC internal to the control panel would read the removable card including uploading executing machine readable program instructions contained thereon for performing any of the functionality described herein.

Directional buttons 703, are shown to enable a variety of functions including increasing/decreasing a volume being played through speaker 704. The up/down buttons may be configured to increase intensities of any of the emitters fixed to an inner side of band 401 or to adjust the sensitivities of any of the sensor elements of the photodetectors. Buttons 704 may be used to tune the present apparatus to standards set by the FDA or other regulatory agencies. USB port 704 enables the connection of a USB cord to the present apparatus. Such a connection can enable any of a variety of functions. For example, the USB device may be used to program a microprocessor or configure the present apparatus specifically to a particular patient and set threshold levels for atrial fibrillation detection and monitoring.

Speaker 705 enables an audible feedback for the visually impaired. Such as an audible alert may be initiated in response to the presence of atrial fibrillation or the detected event being outside a pre-defined limit of acceptability. The audible alert may be varied in volume, frequency, and intensity, as desired, using the up/down buttons 703. LEDs 706 enable any of a variety of visual feedback for the hearing impaired. Visual feedback may take the form of, for instance, a green LED being activated when the device is turned ON. A red LED may be activated in response to an alert condition. A blue LED can be activated when the atrial fibrillation is not present. The LEDs can be activated in response to a communication occurring between the present apparatus and a remote device via a wireless communication protocol. The LEDs may be activated in combination. Button 707 turns the device ON/OFF. The device is capable of wirelessly communicating text, email, picture, graph, chart, and/or a pre-recorded message to a remote device such as, for example, a smartphone, a Wi-Fi router, an I-Pad, a Tablet-PC, a laptop, a computer, and the like. Such communication may utilize a Bluetooth protocol. The communication may utilize network 710 shown as an amorphous cloud.

It should be appreciated that the embodiments described are illustrative for explanatory purposes and are not to be viewed as limiting the scope of the appended claims solely to the elements or configuration of FIG. 7.

Example Flow Diagram

Figure 8:
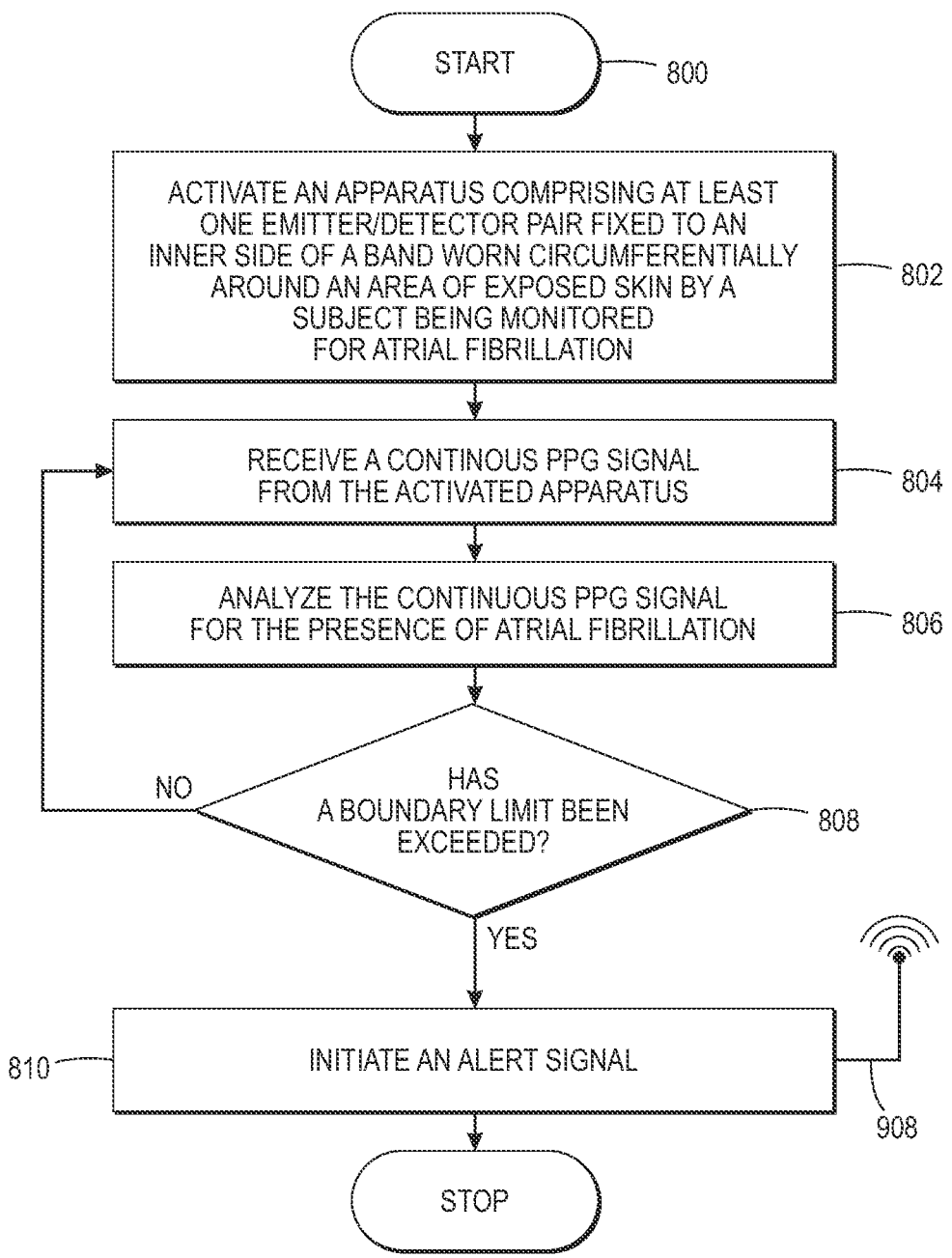
FIG. 8 is a flow diagram of one embodiment of the present method for monitoring a subject of interest for atrial fibrillation.

Reference is now being made to the flow diagram of FIG. 8 which illustrates one embodiment of the present method for monitoring a subject of interest for atrial fibrillation. Flow processing begins at step 800 and immediately proceeds to step 802.

At step 802, activate an apparatus comprising at least one emitter/detector pair fixed to an inner side of a band worn circumferentially around an area of exposed skin by a subject being monitored for the present of atrial fibrillation. The emitter has at least one illuminator with a wavelength band centered about 660 nm or 940 nm. The apparatus may be worn in any of the areas shown in FIGS. 1-3. The apparatus may be any of the transmissive or reflective devices of FIGS. 4 and 5. The device can be activated by the connection of power thereto or by pressing an ON/OFF switch such as Button 707 of FIG. 7. Upon activation, the illuminators emit their source light which, in turn, is sensed by each emitters paired photodetector. A continuous PPG signal is generated thereby.

At step 804, receive a continuous PPG signal from the detectors of the activated apparatus.

At step 806, analyze the continuous PPG signal for atrial fibrillation.

At step 808, a determination is made, as a result of analyzing the PPG signal in step 806, whether a boundary limit has been exceeded. If so then, at step 810, an alert signal is initiated. The alert signal or notification can be sent to a technician, nurse, medical practitioner, and the like, using, for example, antenna 908 (of FIG. 9). In one embodiment, the alert signal is communicated via network 710 of FIG. 7. Such a signal may take the form of a message or, for instance, a bell tone, ring, or sonic alert being activated at a nurse's station. The alert signal may take the form of initiating a visible light which provides an indication such as, for instance, a blinking colored light such as the LEDs 706 of FIG. 7. If, at step 808, a boundary limit has not been exceeded then processing repeats with respect to step 804 wherein the PPG signal is continuously received and analyzed for atrial fibrillation. Processing repeats in a similar manner. In another embodiment, further processing stops. The apparatus hereof is intended to be used for continuous monitoring while the device is ON.

The flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Diagram of Networked System

Figure 9:
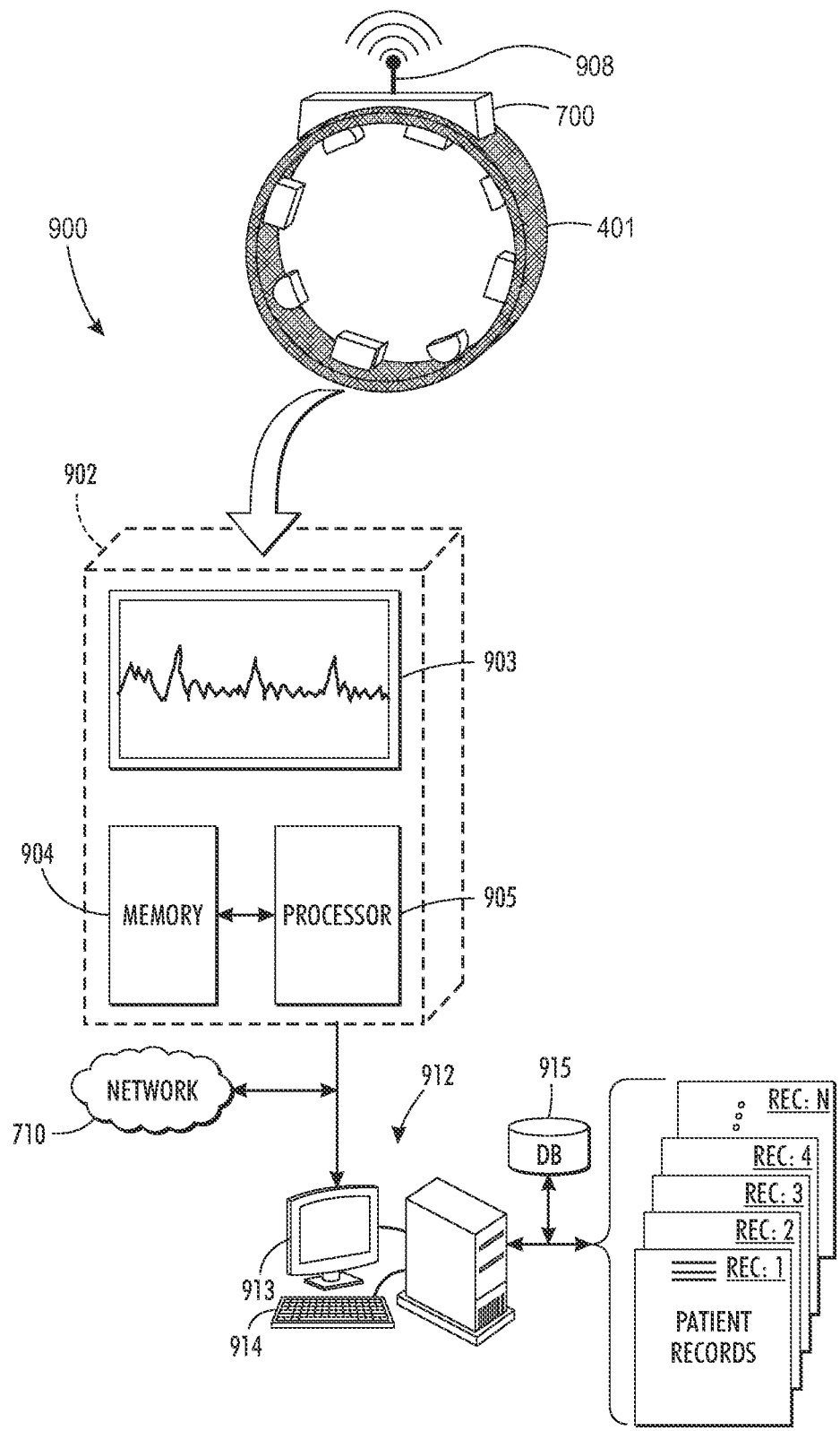
FIG. 9 is a block diagram illustrating one example networked system for performing various aspects of the teachings hereof.

Reference is now being made to FIG. 9 which illustrates a block diagram of one example signal processing system 900 for performing various aspects of the teachings hereof.

In FIG. 9, the control panel 700 of the present apparatus is fixed to band 401 utilizes antenna 908 to communicate a continuous PPG signal to a wireless cellular device 902 which may be a smartphone, i-phone, Android Device, or another wireless cellphone as are widely used and commonly found in various streams of commerce. Smartphone 902 has a display 903, a memory 904, and a processor 905 which executes machine readable program instructions for analyzing the continuous PPG signal or for processing the time-series signal received from the present apparatus to extract the continuous PPG signal. The smartphone may execute applications developed and configured to work with various embodiments of the present transmissive or reflective sensing devices. Downloadable applications for a cellular smartphone 902 may include, for example, a Signal Extractor Application which receives the time-series signal and extracts a physiological signal corresponding to one or more physiological functions which the subject is being monitored for. Another application may be a Signal Compensation Application which processes the PPG signal to compensate for artifacts that may have been introduced therein. A Signal Analyzer Application may be employed to analyze the PPG signal to determine the occurrence of a cardiac event for the subject. An Event Monitoring Application may be used for continuously determining whether the PPG signals are within acceptable limits. Such an application would initiate an alert in response to an A-fib event having occurred or for being outside a boundary of acceptability pre-set for the subject. The Event Monitoring Application may be configured to communicate a message to a remote device such as the cellphone of a medical professional via antenna 908. Such applications may be downloadable from an online AppStore where cellphone applications are often made available.

The networked system of FIG. 9 is shown in communication with a workstation 912 comprising a computer case housing a motherboard, CPU, memory, interface, storage device, and a communications link such as a network card, and having a display device 913 such as a CRT, LCD, or touchscreen display. An alphanumeric keyboard 914 and a mouse (not shown) effectuate a user input. It should be appreciated that the workstation has an operating system and other specialized software configured to display a variety of numeric values, text, scroll bars, pull-down menus with user selectable options, and the like, for entering, selecting, or modifying information. The workstation has a removable media (not shown) and implements a database 915 wherein various patient records are stored. Information obtained using the present apparatus can be uploaded to patient records. Records stored in the database can be indexed, searched, and retrieved in response to a query. Patient information can be stored to any of the records in the database and used for A-fib event monitoring. Although the database is shown as an external device, the database may be internal to the workstation mounted on a hard disk housed in the computer case. The processor 905 and memory 904 of FIG. 9 are in communication with the workstation via pathways (not shown) and may further be in communication with one or more remote devices over network 710. It should be appreciated that some or all of the functionality performed by the smartphone device 902 may be performed, in whole or in part, by the workstation.

Various aspects of the teachings hereof may be practiced in distributed environments where tasks are performed by a plurality of devices linked via a network and may be implemented using any known or later developed systems, structures, devices, or software by those skilled in the applicable arts without undue experimentation from the description provided herein. One or more aspects of the systems and methods described herein are intended to be incorporated in an article of manufacture which may be shipped, sold, leased, or otherwise provided separately either alone or as part of a product suite. The above-disclosed features and functions or alternatives thereof, may be combined into other systems or applications. Presently unforeseen or unanticipated alternatives, modifications, variations, or improvements may become apparent and/or subsequently made by those skilled in the art and, further, may be desirably combined into other different systems or applications. Changes to the above-described embodiments may be made without departing from the spirit and scope of the invention. The teachings of any printed publications including patents and patent applications, are each separately hereby incorporated by reference in their entirety.

What is claimed is:

1. A method for monitoring a subject of interest for atrial fibrillation, the method comprising:
    activating an apparatus comprising one of a transmissive device, or a reflective device, each with a plurality of emitter/detector pairs with at least one illuminator emitting source light at a specified wavelength band, and fixed to an inner side of a band worn circumferentially around an area of exposed skin by a subject of interest being monitored for the presence of cardiac arrhythmia, each detector comprises at least one sensor that is sensitive to a wavelength band of the illuminator, the detector measuring an intensity of received light emitted by an illuminator, said measurements comprising a continuous photoplethysmographic (PPG) signal for said subject, said apparatus comprising a control panel with a LED which is activated when the device is turned ON, an alert LED which is activated in response to an alert condition, a LED which is activated when atrial fibrillation is not present, and a speaker providing an audible alert in response to a presence of atrial fibrillation, said controller
    (i) turning said emitter/detector pairs ON/OFF for a desired length of time,
    (ii) receiving said measured intensities from each of said detectors, and
    (iii) communicating said intensities to a wireless handheld device executing a downloadable application for analyzing said continuous PPG signal measured intensity for a determination of the presence of atrial fibrillation, said wireless handheld device signaling said controller to perform at least one of: turning ON said alert LED to indicate a presence of atrial fibrillation, and emitting a sound through said speaker.

2. The method of claim 1, wherein said cardiac arrhythmia is atrial fibrillation.

3. The method of claim 1, wherein said apparatus is a transmissive device said illuminator and paired detector defines a chord of living tissue through which said emitted source light passes, the detector measuring an intensity of light passing through said chord of living tissue.

4. The method of claim 3, wherein each illuminator is separated from its paired detector by a distance D, said distance being less than 75% of a diametrical distance of the area where said band is being worn, each detector measuring an intensity of light passing through said chord of living tissue.

5. The method of claim 1, wherein said apparatus is a reflective device, distance D is a distance between each illuminator and paired detector as measured around said circumference, said emitted light impacting said skin surface at an angle $\theta_L$, each detector measuring an intensity of light reflecting off a surface of skin at an angle $\theta_R$, where $0°<(\theta_L, \theta_R)<90°$.

6. The method claim 1, further comprising a plurality of illuminators each illuminator separated from its paired detector by a distance D.

7. The method of claim 6, wherein a wavelength band of a first illuminator is centered about 660 nm and a wavelength band of a second illuminator is centered about 940 nm.

8. The method of claim 1, wherein a wavelength band of said illuminator is centered at one of 660 nm or 940 nm.

9. The method of claim 1, wherein multiple emitter/detector pairs are fixed circumferentially around an inner side of said band.

10. The method of claim 1, wherein multiple emitters and multiple detectors form an emitter/detector pair.

11. The method of claim 10, wherein each emitter/detector pair is configured to emit/detect a different wavelength band.

12. The method of claim 1, wherein said peak-to-peak pulse points are detected in the continuous PPG signal using an adaptive threshold technique with successive thresholds being based on variations detected in previous magnitudes of said pulse peaks.

13. The method of claim 1, further comprising using a Poincare diagram of said peak-to-peak pulse dynamics to determining a relationship between consecutive beats.

14. The method of claim 1, further comprising normalizing said peak-to-peak pulse points to a frequency between 60-70 bpm to reduce pulse variations.

15. The method of claim 1, further comprising determining whether a time interval between consecutive beats of said signal is outside an acceptable limit for said subject.

16. The method of claim 1, further comprising communicating said continuous PPG signal measured intensities to any of: a smartphone, a Wi-Fi router, an I-Pad, a Tablet-PC, a laptop, and a computer.

17. The method of claim 1, further comprising initiating an alert signal in response to said cardiac arrhythmia such as atrial fibrillation being outside a pre-defined limit of acceptability.

18. The method of claim 12, wherein said signal comprises any of: text, email, picture, graph, chart, and pre-recorded message.

19. An apparatus for monitoring a subject of interest for cardiac arrhythmia, the apparatus comprising:
    one of a transmissive device or a reflective device, each with a plurality of emitter/detector pairs with at least one illuminator emitting source light at a specified wavelength band, and fixed to an inner side of a band worn circumferentially around an area of exposed skin by a subject of interest being monitored for the presence of cardiac arrhythmia, each detector comprises at least one sensor that is sensitive to a wavelength band of the illuminator, the detector measuring an intensity of received light emitted by an illuminator, said measurements comprising a continuous photoplethysmographic (PPG) signal for said subject, said apparatus comprising a control panel with a LED which is activated when the device is turned ON, an alert LED which is activated in response to an alert condition, a LED which is activated when atrial fibrillation is not present, and a speaker providing an audible alert in response to a presence of atrial fibrillation, said controller (i) turning said emitter/detector pairs ON/OFF for a desired length of time, (ii) receiving said measured intensities from each of said detectors, and (iii)

communicating said intensities to a wireless handheld device executing a downloadable application for analyzing said continuous PPG signal measured intensity for a determination of the presence of atrial fibrillation, said wireless handheld device signaling said controller to perform at least one of: turning ON said alert LED to indicate a presence of atrial fibrillation, and emitting a sound through said speaker.

20. The apparatus of claim 19, wherein said cardiac arrhythmia is atrial fibrillation.

21. The apparatus of claim 19, wherein said apparatus is a transmissive device said illuminator and paired detector defines a chord of living tissue through which said emitted source light passes, the detector measuring an intensity of light passing through said chord of living tissue.

22. The apparatus of claim 21, wherein each illuminator is separated from its paired detector by a distance D, said distance being less than 75% of a diametrical distance of the area where said band is being worn, each detector measuring an intensity of light passing through said chord of living tissue.

23. The apparatus of claim 19, wherein said apparatus is a reflective device, distance D is a distance between each illuminator and paired detector as measured around said circumference, said emitted light impacting said skin surface at an angle $\theta_L$, each detector measuring an intensity of light reflecting off a surface of skin at an angle $\theta_R$, where $0° < (\theta_L, \theta_R) < 90°$.

24. The apparatus of claim 19, further comprising a plurality of illuminators each illuminator separated from its paired detector by a distance D.

25. The apparatus of claim 24, wherein a wavelength band of a first illuminator is centered about 660 nm and a wavelength band of a second illuminator is centered about 940 nm.

26. The apparatus of claim 19, wherein a wavelength band of said illuminator is centered at one of 660 nm or 940 nm.

27. The apparatus of claim 19, wherein multiple emitter/detector pairs are fixed circumferentially around an inner side of said band.

28. The apparatus of claim 19, wherein multiple emitters and multiple detectors form an emitter/detector pair.

29. The apparatus of claim 28, wherein each emitter/detector pair is configured to emit/detect a different wavelength band.

30. The apparatus of claim 19, wherein said peak-to-peak pulse points are detected in the continuous PPG signal using an adaptive threshold technique with successive thresholds being based on variations detected in previous magnitudes of said pulse peaks.

31. The apparatus of claim 19, further comprising using a Poincare diagram of said peak-to-peak pulse dynamics to determining a relationship between consecutive beats.

32. The apparatus of claim 19, further comprising normalizing said peak-to-peak pulse points to a frequency between 60-70 bpm to reduce pulse variations.

33. The apparatus of claim 19, further comprising determining whether a time interval between consecutive beats of said signal is outside an acceptable limit for said subject.

34. The apparatus of claim 19, further comprising communicating said continuous PPG signal measured intensities to any of: a smartphone, a Wi-Fi router, an I-Pad, a Tablet-PC, a laptop, and a computer.

35. The apparatus of claim 19, further comprising initiating an alert signal in response to said cardiac arrhythmia such as atrial fibrillation being outside a pre-defined limit of acceptability.

36. The apparatus of claim 35, wherein said signal comprises any of: text, email, picture, graph, chart, and pre-recorded message.

* * * * *